US008467866B2

(12) United States Patent  
Yanagi et al.

(10) Patent No.: US 8,467,866 B2  
(45) Date of Patent: Jun. 18, 2013

(54) BIOSIGNAL DETECTING APPARATUS (75) Inventors: Masahiro Yanagi, Shinagawa (JP);  
Satoshi Sakurai, Shinagawa (JP);  
Shigemi Kurashima, Shinagawa (JP);  
Takashi Arita, Shinagawa (JP)

(73) Assignee: Fujitsu Component Limited, Tokyo (JP)

( * ) Notice: Subject to any disclaimer, the term of this patent is extended or adjusted under 35 U.S.C. 154(b) by 815 days.

(21) Appl. No.: 12/216,535

(22) Filed: Jul. 7, 2008

(65) Prior Publication Data  
US 2009/0234216 A1  Sep. 17, 2009

(30) Foreign Application Priority Data  
Mar. 13, 2008 (JP) ................... 2008-063770

(51) Int. Cl.  
*A61B 5/00* (2006.01)

(52) U.S. Cl.  
USPC ........................................ 600/547

(58) Field of Classification Search  
USPC ............... 340/124; 600/547, 544, 545  
See application file for complete search history.

(56) References Cited

U.S. PATENT DOCUMENTS

| | | | | |
|---|---|---|---|---|
| 5,335,664 | A | * | 8/1994 | Nagashima ................. 600/508 |
| 7,783,344 | B2 | * | 8/2010 | Lackey et al. ............... 600/547 |
| 2004/0167421 | A1 | * | 8/2004 | Gregory et al. ............. 600/547 |
| 2007/0270665 | A1 | * | 11/2007 | Yang et al. .................. 600/300 |
| 2008/0262376 | A1 | * | 10/2008 | Price ........................... 600/547 |
| 2009/0024044 | A1 | * | 1/2009 | Virtanen et al. ............. 600/509 |

FOREIGN PATENT DOCUMENTS

JP  5-317278  12/1993

* cited by examiner

*Primary Examiner* — Max Hindenburg  
(74) *Attorney, Agent, or Firm* — Staas & Halsey LLP

(57) ABSTRACT

A biosignal detecting apparatus is disclosed. The biosignal detecting apparatus includes a pair of detecting electrodes which is attached to a human body for detecting a biosignal from the human body, a biosignal detecting circuit which receives the biosignal detected by the detecting electrodes and processes the detected biosignal, a transmitting electrode which is attached to the human body for transmitting the biosignal processed by the biosignal detecting circuit via the human body to an external apparatus and for transmitting a radio wave generated by a circuit in the biosignal detecting apparatus, and a circuit connected to one of the detecting electrodes which circuit receives the radio wave transmitted from the human body via the transmitting electrode and executes impedance matching between the biosignal detecting apparatus and the human body based on the received radio wave transmitted from the human body via the transmitting electrode.

20 Claims, 5 Drawing Sheets

BIOSIGNAL DETECTING APPARATUS

BACKGROUND OF THE INVENTION

1. Field of the Invention

The present invention generally relates to a biosignal detecting apparatus which executes communications by using a human body as an antenna.

2. Description of the Related Art

Recently, a very short distance radio communication network has been proposed in the fields of medical services and healthcare. This network is called a BAN (body area network), and communications standards of the BAN have been proposed in which a body embedded type instrument or a wearable type instrument is used in the BAN.

In addition, conventionally, instead of using the BAN, technologies using a human body as an antenna have been proposed. For example, an apparatus is disclosed in Patent Document 1. In the apparatus, an electric signal corresponding to human body information is detected from the skin part of a human body, the detected signal is converted into a high frequency signal, and the high frequency signal is transmitted to another apparatus by using the human body as the antenna.

[Patent Document 1] Japanese Laid-Open Patent Application No. 5-317278

However, the human body has a property of absorbing electromagnetic waves (radio waves), and when the human body is used as an antenna, a loss of the electromagnetic waves occurs and the electromagnetic waves may be changed. In addition, conditions for obtaining impedance matching between the apparatus and the human body are changed depending on a relationship between a wavelength of a used electromagnetic wave and the body height of a person or positions of electrodes attached to the human body. Especially, the conditions for obtaining the impedance matching are remarkably changed when the human body is moved.

However, conventionally, when the human body is used as an antenna, the impedance matching between the human body and the apparatus has not been obtained under conditions where elements such as a loss of the electromagnetic waves to be transmitted and a body height difference among individuals are assumed.

SUMMARY OF THE INVENTION

The present invention may provide a biosignal detecting apparatus which can obtain impedance matching between a human body and an apparatus when the human body is used as an antenna.

According to one aspect of the present invention, there is provided a biosignal detecting apparatus. The biosignal detecting apparatus includes a pair of detecting electrodes which is attached to a human body for detecting a biosignal from the human body, a biosignal detecting circuit which receives the biosignal detected by the detecting electrodes and processes the detected biosignal, a transmitting electrode which is attached to the human body for transmitting the biosignal processed by the biosignal detecting circuit via the human body to an external apparatus and for transmitting a radio wave generated by a circuit in the biosignal detecting apparatus, and a circuit connected to one of the detecting electrodes which circuit receives the radio wave transmitted from the human body via the transmitting electrode and executes impedance matching between the biosignal detecting apparatus and the human body based on the received radio wave transmitted from the human body via the transmitting electrode.

According to another aspect of the present invention, there is provided a biosignal detecting apparatus. The biosignal detecting apparatus includes a pair of detecting electrodes which is attached to a human body for detecting a biosignal from the human body, a biosignal detecting circuit which receives the biosignal detected by the detecting electrodes and processes the detected biosignal, a transmitting electrode which is attached to the human body for transmitting the biosignal processed by the biosignal detecting circuit via the human body to an external apparatus and for transmitting a radio wave generated by a circuit in the biosignal detecting apparatus, and a circuit connected to one of the detecting electrodes which circuit receives the radio wave transmitted from the human body via the transmitting electrode and optimizes a frequency or output power of a carrier of the biosignal to be transmitted to the external device based on the received radio wave transmitted from the human body via the transmitting electrode.

According to another aspect of the present invention, the transmitting electrode is formed of a pair of electrodes for diversity transmission.

According to another aspect of the present invention, the electrodes for the diversity transmission are installed in corresponding headphones of a headphone set, corresponding earphones of an earphone set, a frame of a pair of glasses, a wristband, corresponding straps of wear, a belt, a cap, or a helmet.

According to an embodiment of the present invention, since a biosignal detecting apparatus includes a circuit for obtaining impedance matching between the biosignal detecting apparatus and a human body, when the human body is used as an antenna, the impedance matching between the biosignal detecting apparatus and the human body can be obtained.

Features and advantages of the present invention will be apparent from the following detailed description when read in conjunction with the accompanying drawings.

DESCRIPTION OF THE PREFERRED EMBODIMENTS

Referring to the drawings, embodiments of the present invention are described.

First Embodiment

Figure 1:
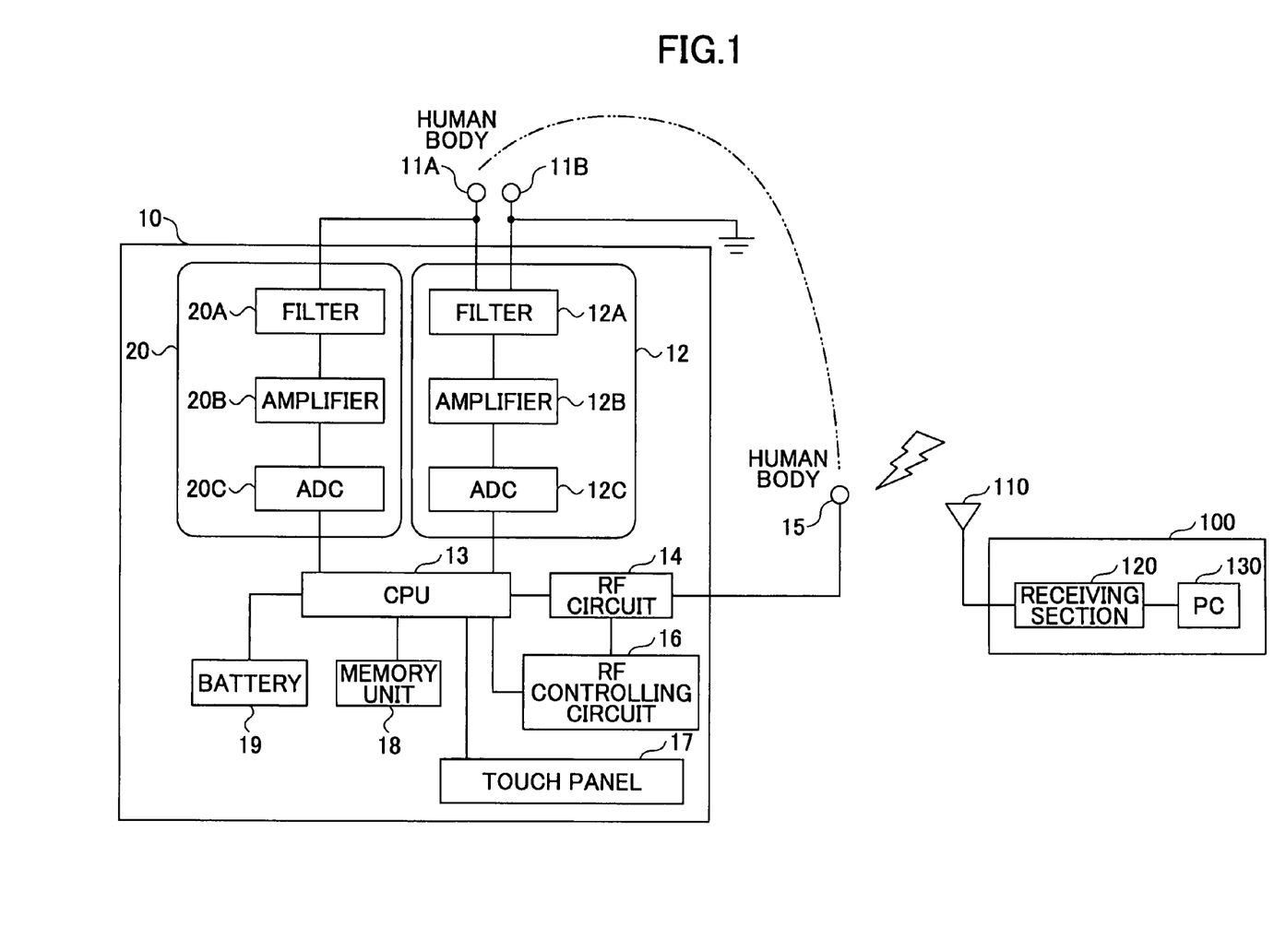
FIG. 1 is a diagram showing a hardware structure of a biosignal detecting apparatus according to a first embodiment of the present invention.

FIG. 1 is a diagram showing a hardware structure of a biosignal detecting apparatus 10 according to a first embodiment of the present invention. In FIG. 1, in addition to the biosignal detecting apparatus 10, a processing apparatus 100 (external apparatus) which receives a biosignal transmitted from the biosignal detecting apparatus 10 is shown.

As shown in FIG. 1, the biosignal detecting apparatus 10 according to the first embodiment of the present invention includes a pair of detecting electrodes 11A and 11B which electrodes detect a biosignal in contact with the skin parts of a human body, a biosignal detecting circuit 12, a CPU (central processing unit) 13, an RF (radio frequency) circuit 14, a transmitting electrode 15 connected to the RF circuit 14, an RF controlling circuit 16, a touch panel 17, a memory unit 18, a battery 19, and an RF signal detecting circuit 20.

The detecting electrodes 11A and 11B are connected to the biosignal detecting circuit 12. In addition, the detecting electrode 11A is connected to the RF signal detecting circuit 20, and the detecting electrode 11B is connected to ground potential.

The biosignal detecting circuit 12 includes a filter 12A, an amplifier 12B, an ADC (analog to digital converter) 12C, and the biosignal detecting circuit 12 is connected to the CPU 13. In addition, the RF circuit 14, the RF controlling circuit 16, the touch panel 17, the memory unit 18, the battery 19, and the RF signal detecting circuit 20 are connected to the CPU 13. The transmitting electrode 15 is connected to the CPU 13 via the RF circuit 14.

The biosignal detecting apparatus 10 detects a biosignal, processes the detected biosignal, and transmits the processed biosignal, by using a carrier in which the processed biosignal is modulated, to the processing apparatus 100 at a position away from the human body whose biosignal is detected by the biosignal detecting apparatus 10. The processing apparatus 100 includes a receiving antenna 110, a receiving section 120, and a PC (personal computer) 130. The transmitted biosignal is received at the receiving antenna 110, the received biosignal is demodulated at the receiving section 120, and the biosignal is extracted. The extracted biosignal is input to the PC 130. The PC 130 processes the received biosignal for making a diagnosis of a person's disease.

The detecting electrodes 11A and 11B detect, for example, brain waves (biosignal) of a person by being attached to predetermined corresponding positions of the head of the person. The detecting electrode 11A also receives an RF signal (radio wave) transmitted from the transmitting electrode 15 in addition to receiving the brain waves. The RF signal transmitted from the transmitting electrode is described below in detail. The brain waves can be detected by using the Montreal Method.

The brain waves (biosignal) detected by the detecting electrodes 11A and 11B are processed by the biosignal detecting circuit 12 and the processed biosignal is stored in the memory unit 18 as biological data. The stored biological data are transmitted to the processing apparatus 100 based on operations of a user on the touch panel 17 via the RF circuit 14 and the transmitting electrode 15 by using the human body as the antenna under control of the CPU 13. At this time, the detecting electrode 11A also receives an RF signal (radio wave) for obtaining impedance matching transmitted from the transmitting electrode 15 by using the human body as the antenna.

In the above, in the biosignal detecting apparatus 10, the timing of the brain waves (biosignal) detecting process at the detecting electrodes 11A and 11b is different from the timing of the RF signal (radio wave) receiving process at the detecting electrode 11A via the transmitting electrode 15 by using the human body as the antenna. That is, the brain waves (biosignal) are prevented from being added to the RF signal transmitted from the transmitting electrode 15 at the detecting electrode 11A.

Next, the biosignal detecting circuit 12 is described in detail.

The filter 12A is a band pass filter which removes unnecessary components such as noise from the biosignal detected by the detecting electrodes 11A and 11B. The biosignal whose unnecessary components are removed is amplified by the amplifier 12B and the amplified biosignal is converted into a digital signal by the ADC 12C and the converted signal is output as the biological data.

The CPU 13 controls and executes the following processes based on an instruction of a user on the touch panel 17. That is, the processes include a transmitting process of the biosignal (biosignal transmitting process) via the RF circuit 14 and the transmitting electrode 15 to the processing apparatus 100, an adjusting process of the frequency of the carrier at the RF circuit 14, a biosignal detecting process, an impedance matching process, a displaying process of the biological data (biosignal) on the touch panel 17, a biological data (biosignal) storing (writing) process in the memory unit 18, and a biological data (biosignal) reading process from the memory unit 18.

The RF circuit 14 converts the digital biological data read by the CPU 13 from the memory unit 18 into analog biological data (biosignal), modulates the analog biological data on a carrier, and outputs the modulated analog biological data.

The transmitting electrode 15 is attached to the skin part of the human body and transmits the biosignal and the RF signal (radio wave) from the RF circuit 14 by using the human body as an antenna. In this, the transmitting electrode 15 is attached to the skin part of the human body by using, for example, a belt or a clip. The transmitting electrode 15 and the detecting electrodes 11A and 11B are attached to the same person.

The RF controlling circuit 16 optimizes the frequency of the carrier which is used by the RF circuit 14 based on an RF signal detected by the RF signal detecting circuit 20 so that the impedance matching is obtained, based on the RF signal detected by the RF signal detecting circuit 20. The RF signal detecting circuit 20 is described below in detail.

The touch panel 17 displays operating buttons and receives an instruction from a user when the user touches an operating button, and also displays the biological data which are sent from the biosignal detecting circuit 12 to the CPU 13 and the biological data stored in the memory unit 18.

The touch panel 17 is formed of, for example, an LCD (liquid crystal display) and a matrix switch. The user can instruct the biosignal detecting apparatus 10 to execute a process by touching an operating button on the touch panel 17.

In addition, the biosignal detecting apparatus 10 can further include LEDs (light emitting diodes) for showing the level of the biosignal and a speaker for informing the user of the progress of a process.

The memory unit 18 stores the biological data and can be a non-volatile solid-state memory unit.

The battery 19 supplies power to the elements in the biosignal detecting apparatus 10 via the CPU 13, and is, for example, a lithium battery.

The RF signal detecting circuit 20 is connected to the detecting electrode 11A and the CPU 13. The RF signal detecting circuit 20 includes a filter 20A, an amplifier 20B, and an ADC 20C.

The filter 20A is a band pass filter which removes unnecessary components such as noise from the RF signal for impedance matching detected by the detecting electrode 11A. The RF signal whose unnecessary components are removed is amplified by the amplifier 20B, the amplified RF signal is converted into a digital signal by the ADC 20C, and the converted signal is output from the ADC 20C.

That is, in the biosignal detecting apparatus 10, when the detecting electrode 11A receives an RF signal transmitted from the transmitting electrode 15 by using the human body as the antenna, unnecessary components such as noise are removed from the received RF signal by the filter 20A; the RF signal whose unnecessary components is removed is amplified by the amplifier 20B, the amplified RF signal is converted into a digital signal, and the digital signal is output.

When the transmitting electrode 15 is attached to a human body, since there is a difference among individuals such as a height difference and a weight difference, resonance frequencies of the human body and the biosignal detecting apparatus 10 must be adjusted.

The CPU 13 determines whether the impedance matching is obtained between the biosignal detecting apparatus 10 (the transmitting electrode 15) and the human body based on the level of a signal input from the RF signal detecting circuit 20. When the impedance matching is not obtained, the CPU 13 obtains the impedance matching between the biosignal detecting apparatus 10 (the transmitting electrode 15) and the human body by causing the RF controlling circuit 16 to adjust the capacitance value of a variable capacitor or a variable capacitance diode in the RF circuit 14.

Figure 2:
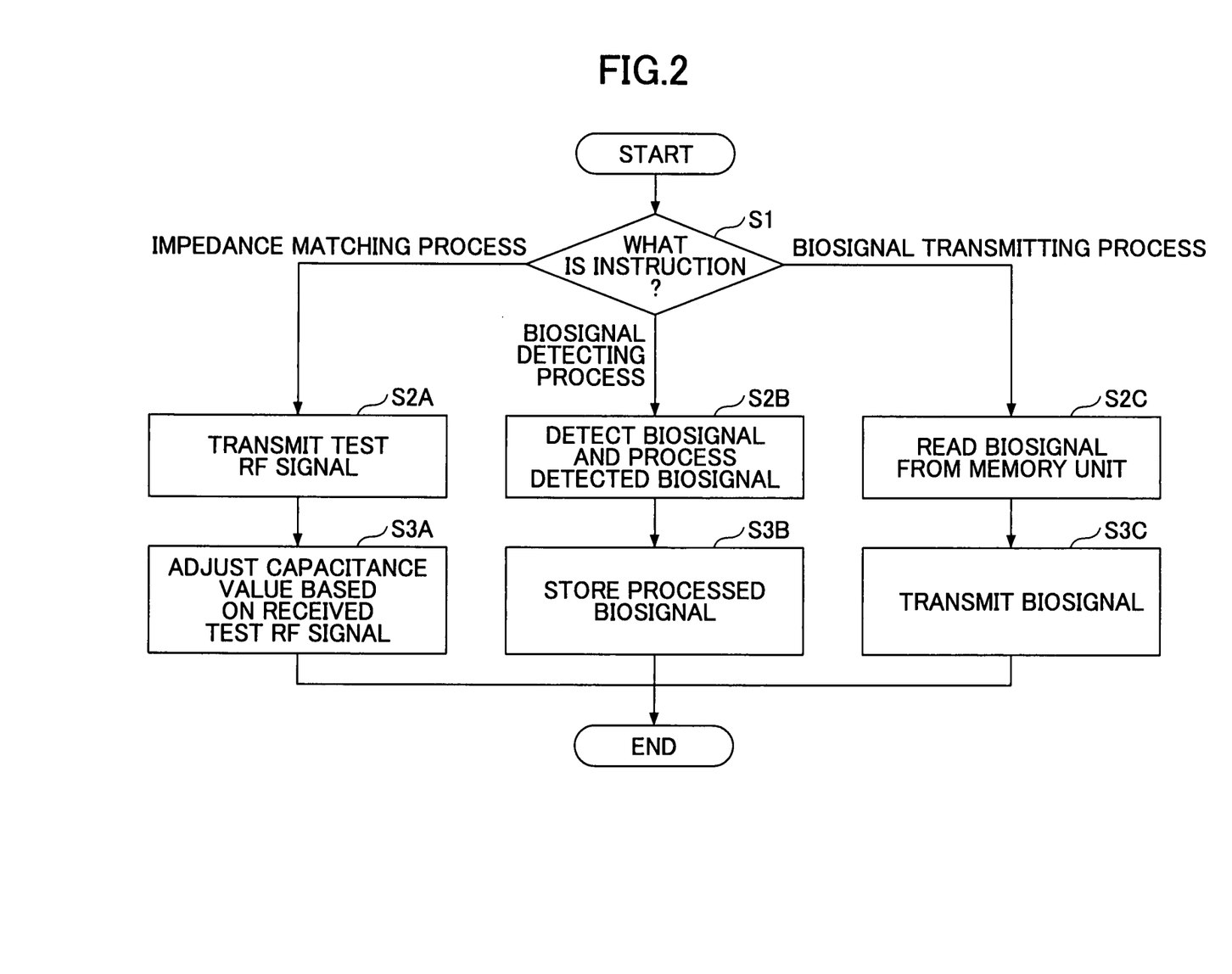
FIG. 2 is a flowchart showing an impedance matching process, a biosignal detecting process, and a biosignal transmitting process by a CPU shown in FIG. 1.

FIG. 2 is a flowchart showing the impedance matching process, the biosignal detecting process, and the biosignal transmitting process by the CPU 13.

Referring to FIG. 2, the processes are described.

First, the CPU 13 recognizes an instruction by a user input on the touch panel 17 (S1).

When the CPU 13 recognizes that the instruction is to execute the impedance matching process, the CPU 13 causes the RF circuit 14 to transmit a test RF signal (radio wave) via the transmitting electrode 15 (S2A).

When the detecting electrode 11A receives the test RF signal, the CPU 13 obtains the impedance matching between the biosignal detecting apparatus 10 (the transmitting electrode 15) and the human body by causing the RF controlling circuit 16 to adjust the capacitance value of a variable capacitor or a variable capacitance diode in the RF circuit 14 based on the received test RF signal via the RF signal detecting circuit 20 (S3A). With this, the impedance matching process ends.

When the CPU 13 recognizes that the instruction is to execute the biosignal detecting process, the CPU 13 causes the detecting electrodes 11A and 11B to detect a biosignal and causes the biosignal detecting circuit 12 to process the detected biosignal (S2B).

The CPU 13 stores the biosignal processed by the biosignal detecting circuit 12 into the memory unit 18 as biological data (S3B). With this, the biosignal detecting process ends.

When the CPU 13 recognizes that the instruction is to execute the biosignal transmitting process, the CPU 13 reads the biosignal (biological data) from the memory unit 18 (S2C).

The CPU 13 transmits the read biosignal to the processing apparatus 100 via the RF circuit 14, and the transmitting electrode 15 by using the human body as the antenna (S3C). With this, the biosignal transmitting process ends.

In FIG. 2, the biosignal (biological data) displaying process on the touch panel 17 is omitted. However, when the CPU 13 recognizes that the instruction is to execute the biosignal displaying process, the CPU 13 displays the biosignal (biological data) in the memory unit 18 on the touch panel 17. In this case, a waveform of the biosignal (biological data) is displayed on the touch panel 17.

As described above, according to the biosignal detecting apparatus 10 in the first embodiment of the present invention, when a biosignal (biological data) is transmitted to the processing apparatus 100 by using the human body as the antenna, a test RF signal is transmitted to the detecting electrode 11A, and the capacitance value of the variable capacitor or the variable capacitance diode in the RF circuit 14 is adjusted so that the impedance matching is obtained between the biosignal detecting apparatus 10 (the transmitting electrode 15) and the human body. Therefore, a loss of radio waves in the human body can be minimized.

In the above, the detecting electrode 11A is connected to the RF signal detecting circuit 20. However, the detecting electrode 11B can be connected to the RF signal detecting circuit 20. That is, one of the detecting electrodes 11A and 11B is connected to the RF signal detecting circuit 20.

In addition, in the above, when the resonance frequency of the human body is different from the resonance frequency of the biosignal detecting apparatus 10, the impedance matching process is applied. However, instead of applying the impedance matching process, or adding the impedance matching process to a method, the resonance frequency of the human body can be made equal to the resonance frequency of the biosignal detecting apparatus 10 by adjusting the frequency or the output power of the carrier in the RF circuit 14.

Second Embodiment

Next, referring to the drawings, a second embodiment of the present invention is described. In the second embodiment of the present invention, when an element is similar to or the same as that in the first embodiment of the present invention, the same reference number as that in the first embodiment of the present invention is used for the element, and the same description as that in the first embodiment of the present invention is omitted.

Figure 3:
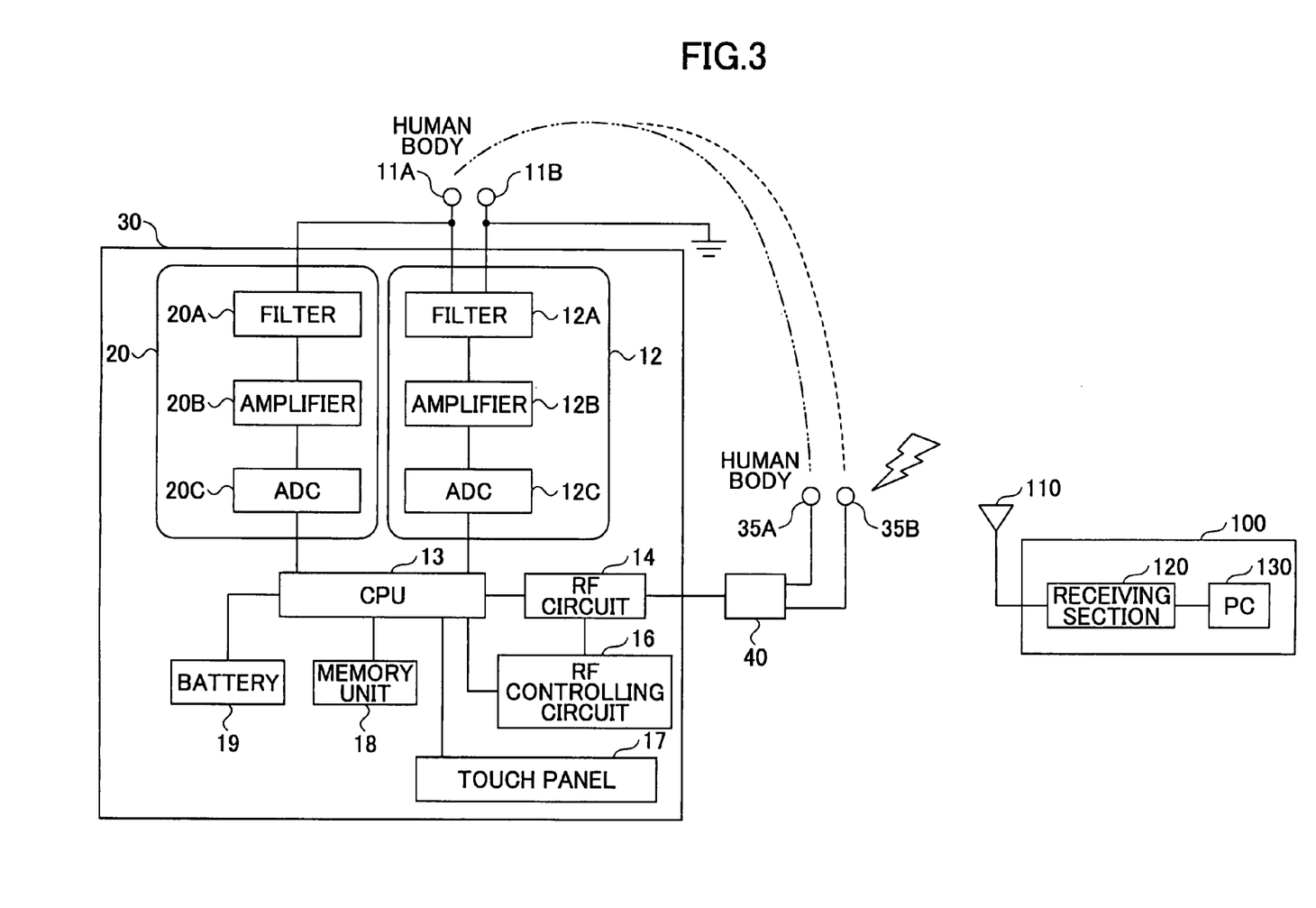
FIG. 3 is a diagram showing a hardware structure of a biosignal detecting apparatus according to a second embodiment of the present invention.

FIG. 3 is a diagram showing a hardware structure of a biosignal detecting apparatus 30 according to the second embodiment of the present invention. In FIG. 3, similar to FIG. 1, the processing apparatus 100 which receives a biosignal transmitted from the biosignal detecting apparatus 30 is shown.

As shown in FIG. 3, when the hardware structure shown in FIG. 3 is compared with the hardware structure shown in FIG. 1, the biosignal detecting apparatus 30 in the second embodiment of present invention includes a pair of transmitting electrodes 35A and 35B instead of using the transmitting electrode 15 shown in FIG. 1, and further includes a divider 40. The pair of the transmitting electrodes 35A and 35B is provided for diversity transmission, and is connected to the RF circuit 14 via the divider 40.

Since the divider 40 is provided, even if the pair of the transmitting electrodes 35A and 35B is used, the impedance matching similar to that in the first embodiment of the present invention can be obtained.

In the biosignal detecting apparatus 30, when a biosignal is transmitted to the processing apparatus 100, since the human body becomes a diversity antenna by the pair of the transmitting electrodes 35A and 35B, the communications quality to the processing apparatus 100 can be improved.

Figure 4:
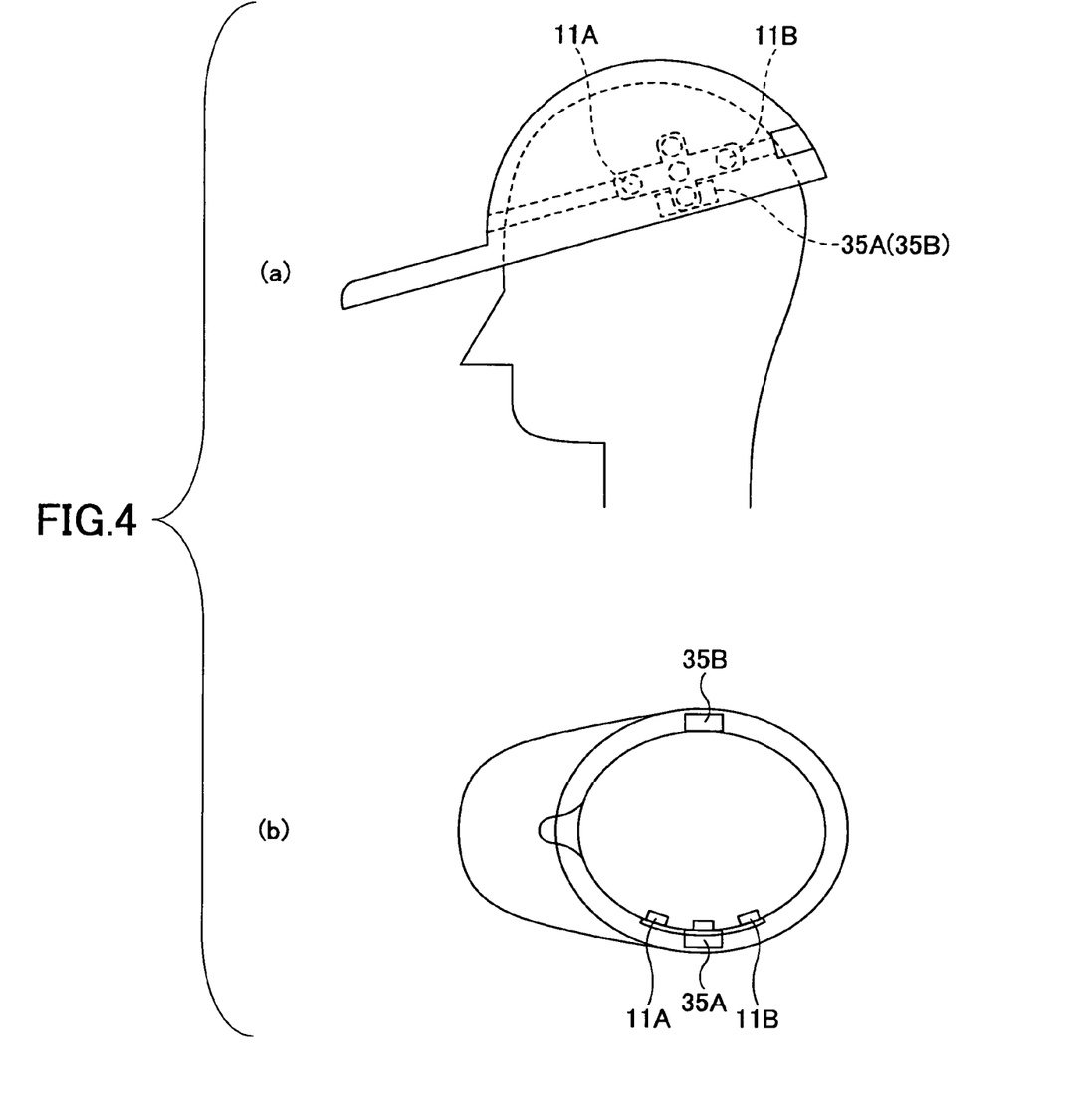
FIG. 4 is a diagram showing a first installing structure of a pair of transmitting electrodes in the biosignal detecting apparatus shown in FIG. 3.

FIG. 4 is a diagram showing a first installing structure of the pair of the transmitting electrodes 35A and 35B in the biosignal detecting apparatus 30 shown in FIG. 3. In FIG. 4, only a part of the biosignal detecting apparatus 30 is shown.

In FIG. 4, (a) shows a side view and (b) shows a top view. As shown in FIG. 4(a), the pair of the transmitting electrodes 35A and 35B is installed in a cap and a human body puts on the cap. In addition, as shown in FIGS. 4(a) and 4(b), the transmitting electrodes 35A and 35B are at the corresponding insides of the cap. When the human body puts on the cap, since the transmitting electrodes 35A and 35B contact the corresponding skin parts of the human body, the human body can function as a diversity antenna.

In addition, as shown in FIGS. 4(a) and 4(b), the detecting electrodes 11A and 11B can be installed in the cap. When the detecting electrodes 11A and 11B are installed in the cap, a biosignal can be detected (measured) and the detected biosignal can be transmitted while the human body wears the cap.

Figure 5A:
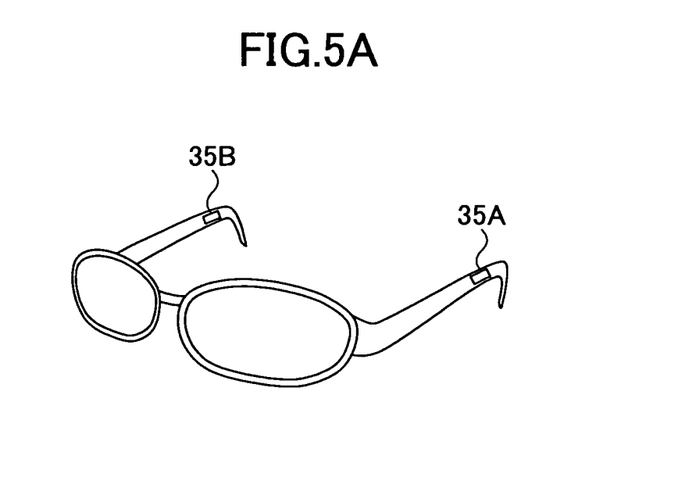
FIG. 5A is a diagram showing a second installing structure of the pair of the transmitting electrodes in the biosignal detecting apparatus shown in FIG. 3.

FIG. 5A is a diagram showing a second installing structure of the pair of the transmitting electrodes 35A and 35B in the biosignal detecting apparatus 30 shown in FIG. 3. In FIG. 5A, only a part of the biosignal detecting apparatus 30 is shown.

As shown in FIG. 5A, the transmitting electrodes 35A and 35B are installed in the corresponding insides of the frame of a pair of glasses. When the human body puts on the glasses, since the transmitting electrodes 35A and 35B contact the corresponding skin parts of the human body, the human body can function as the diversity antenna.

Figure 5B:
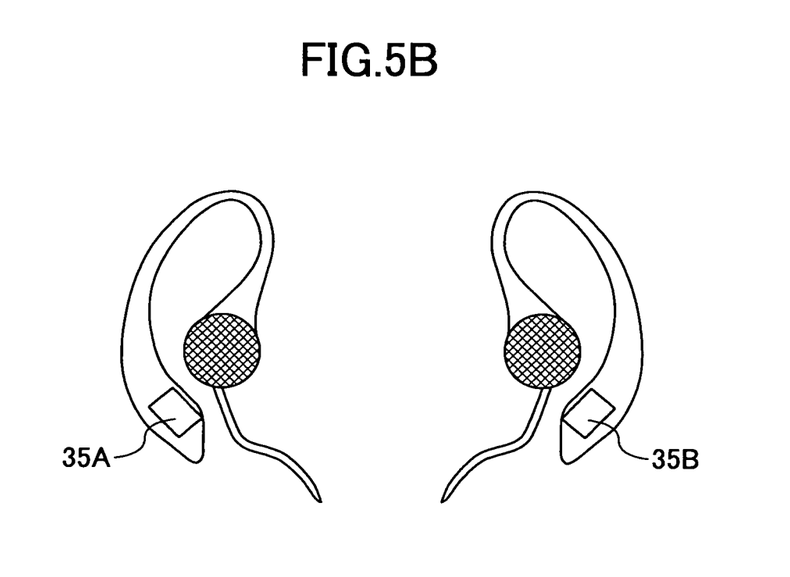
FIG. 5B is a diagram showing a third installing structure of the pair of the transmitting electrodes in the biosignal detecting apparatus shown in FIG. 3.

FIG. 5B is a diagram showing a third installing structure of the pair of the transmitting electrodes 35A and 35B shown in the biosignal detecting apparatus 30 shown in FIG. 3. In FIG. 5B, only a part of the biosignal detecting apparatus 30 is shown.

As shown in FIG. 5B, the transmitting electrodes 35A and 35B are installed at the corresponding insides of the frame of a pair of earphones. When the human body puts on the earphones, since the transmitting electrodes 35A and 35B contact the corresponding skin parts of the human body, the human body can function as the diversity antenna.

As described above, according to the biosignal detecting apparatus 30 in the second embodiment of the present invention, when a person puts on a cap, glasses, or earphones in which the transmitting electrodes 35A and 35B are installed the human body of the person can function as a diversity antenna, and a biosignal detected by the biosignal detecting apparatus 30 can be transmitted to the processing apparatus 100.

In the above, the transmitting electrode 35A and 35B are installed in one of the cap, the frame of the glasses, and the frame of the earphones; however, the transmitting electrodes 35A and 35B can be installed in other wearable objects such as a pair of headphones, a pair of straps of wear, a wristband, a belt, and a helmet.

Further, the present invention is not limited to the specifically disclosed embodiments, and variations and modifications may be made without departing from the scope of the present invention.

The present application is based on Japanese Priority Patent Application No. 2008-063770 filed on Mar. 13, 2008, with the Japanese Patent Office, the entire contents of which are hereby incorporated herein by reference.

What is claimed is:
1. A biosignal detecting apparatus, comprising:
a pair of detecting electrodes configured to be attached directly to human skin of a human body and configured to detect a biosignal from the human body;
a biosignal detecting circuit configured to receive the biosignal detected by the detecting electrodes and configured to process the detected biosignal;
a transmitting electrode configured to transmit the biosignal processed by the biosignal detecting circuit to an external apparatus provided away and remote from the human body and configured to transmit a radio wave directly to a first of the pair of detecting electrodes, the radio wave being generated by a circuit in the biosignal detecting apparatus, when the transmitting electrode is configured to be directly attached to human skin of the human body; and
a circuit connected to the first of the pair of the detecting electrodes configured to receive the radio wave transmitted from the human body via the transmitting electrode and configured to execute impedance matching between the biosignal detecting apparatus and the human body based on the received radio wave transmitted from the human body via the transmitting electrode, wherein a capacitance value of the circuit is adjusted based on a radio wave test signal.

2. The biosignal detecting apparatus as claimed in claim 1, wherein: the transmitting electrode is formed of a pair of electrodes for diversity transmission.

3. The biosignal detecting apparatus as claimed in claim 2, wherein: the electrodes for the diversity transmission are installed in one of corresponding headphones of a headphone set, corresponding earphones of an earphone set, a frame of a pair of glasses, a wristband, corresponding straps of wear, a belt, a cap, and a helmet.

4. The biosignal detecting apparatus as claimed in claim 1, wherein a second of the pair of detecting electrodes is connected to ground.

5. The biosignal detecting apparatus as claimed in claim 1, wherein the biosignal is prevented from being added to the radio wave transmitted by the transmitting electrode to the first of the pair of the detecting electrodes.

6. The biosignal detecting apparatus as claimed in claim 1, wherein the detecting electrodes and the transmitting electrode are each configured to be attached to the same human body.

7. The biosignal detecting apparatus as claimed in claim 1, wherein the impedance matching is performed by adjusting a capacitance in the circuit.

8. A biosignal detecting apparatus, comprising:
a pair of detecting electrodes configured to be attached directly to human skin of a human body and configured to detect a biosignal from the human body, wherein the biosignal is a signal representing brain waves of the human body;
a biosignal detecting circuit configured to receive the biosignal detected by the detecting electrodes and configured to process the detected biosignal, including a band pass filter configured to remove noise components from the biosignal detected by the detecting electrodes;
a transmitting electrode configured to transmit the biosignal processed by the biosignal detecting circuit to an external apparatus provided away and remote from the human body and configured to transmit a radio wave directly to a first of the pair of detecting electrodes, the radio wave being generated by a circuit in the biosignal detecting apparatus, when the transmitting electrode is configured to be directly attached to human skin of the human body; and
a circuit directly connected to the first of the pair of the detecting electrodes configured to receive the radio wave transmitted from the human body via the transmitting electrode and configured to adjust a frequency or output power of a carrier of the biosignal to be transmitted to the external device based on the received radio wave transmitted from the human body via the transmitting electrode, wherein a capacitance value of the circuit is adjusted based on a radio wave test signal.

9. The biosignal detecting apparatus as claimed in claim 8, wherein: the transmitting electrode is formed of a pair of electrodes for diversity transmission.

10. The biosignal detecting apparatus as claimed in claim 9, wherein: the electrodes for the diversity transmission are installed in one of corresponding headphones of a headphone set, corresponding earphones of an earphone set, a frame of a pair of glasses, a wristband, corresponding straps of wear, a belt, a cap, and a helmet.

11. The biosignal detecting apparatus as claimed in claim 8, wherein a second of the pair of detecting electrodes is connected to ground.

12. The biosignal detecting apparatus as claimed in claim 8, wherein the biosignal is prevented from being added to the radio wave transmitted by the transmitting electrode to the first of the pair of the detecting electrodes.

13. The biosignal detecting apparatus as claimed in claim 8, wherein the detecting electrodes and the transmitting electrode are each configured to be attached to the same human body.

14. The biosignal detecting apparatus as claimed in claim 8, wherein the frequency or output power of a carrier of the biosignal is adjusted by making a resonance frequency of the human body equal to a resonance frequency of the biosignal detecting apparatus.

15. A biosignal detecting method, comprising:
detecting a biosignal from a human body with a pair of detecting electrodes configured to be directly attached to human skin of the human body;
receiving the detected biosignal and processing the detected biosignal;
transmitting the processed biosignal, using a transmitting electrode attached to the human body, to an external apparatus provided away and remote from the human body;
transmitting a radio wave, using the transmitting electrode configured to be directly attached to human skin of the human body, directly to a first of the pair of detecting electrodes; and
receiving the radio wave transmitted from the human body via the transmitting electrode and executing an impedance matching between the internal apparatus and the human body based on the received radio wave transmitted from the human body via the transmitting electrode,
wherein a capacitance value of the internal apparatus is adjusted based on a radio wave test signal.

16. The biosignal detecting method as claimed in claim 15, comprising:
forming the transmitting electrode from a pair of electrodes for diversity transmission.

17. The biosignal detecting method as claimed in claim 16, comprising: installing the pair of electrodes for the diversity transmission in one of corresponding headphones of a headphone set, corresponding earphones of an earphone set, a frame of a pair of glasses, a wristband, corresponding straps of wear, a belt, a cap, and a helmet.

18. The biosignal detecting method as claimed in claim 15, comprising: connecting another a second of the pair of the detecting electrodes to ground.

19. The biosignal detecting method as claimed in claim 15, comprising:
preventing the biosignal from being added to the radio wave transmitted by the transmitting electrode to the first of the pair of the detecting electrodes.

20. The biosignal detecting method as claimed in claim 15, comprising:
configuring each of the detecting electrodes and the transmitting electrode to be attached to the same human body.

* * * * *

UNITED STATES PATENT AND TRADEMARK OFFICE
CERTIFICATE OF CORRECTION

PATENT NO. : 8,467,866 B2  
APPLICATION NO. : 12/216535  
DATED : June 18, 2013  
INVENTOR(S) : Masahiro Yanagi et al.

Page 1 of 1

It is certified that error appears in the above-identified patent and that said Letters Patent is hereby corrected as shown below:

In the Claims

Column 8, Line 33, In Claim 4, after "to" insert -- an electrical --.

Column 9, Line 19, In Claim 11, after "to" insert -- an electrical --.

Column 10, Line 27, In Claim 18, after "connecting" delete "another".

Column 10, Line 28, In Claim 18, after "to" insert -- an electrical --.

Signed and Sealed this  
Fifteenth Day of October, 2013

Teresa Stanek Rea  
*Deputy Director of the United States Patent and Trademark Office*